United States Patent [19]

Taylor, Jr.

[11] Patent Number: 4,694,003
[45] Date of Patent: Sep. 15, 1987

[54] METHOD OF TREATING DEPRESSION WITH 5-(AMINOALKYL)-11-PHENYL-5H-DIBENZO(B,E)(1,4) DIAZEPINES

[75] Inventor: Chandler R. Taylor, Jr., Mechanicsville, Va.

[73] Assignee: A. H. Robins Company, Incorporated, Richmond, Va.

[21] Appl. No.: 403,757

[22] Filed: Jul. 30, 1982

Related U.S. Application Data

[63] Continuation-in-part of Ser. No. 305,076, Sep. 24, 1981, abandoned.

[51] Int. Cl.$^4$ .............................................. A61K 31/55
[52] U.S. Cl. .................................. 514/220; 540/471; 548/477
[58] Field of Search ................ 424/244; 260/239 DD; 514/244

[56] References Cited

U.S. PATENT DOCUMENTS

3,347,849  10/1967  Schmutz et al. ............ 260/239 DD

FOREIGN PATENT DOCUMENTS

48-11110  4/1973  Japan ............................ 260/239 DD
907646  10/1962  United Kingdom ........ 260/239 DD
959994  6/1964  United Kingdom ........ 260/239 DD

OTHER PUBLICATIONS

M. Grieg et al., Chem. Abstracts 74:74869q (1971).

Primary Examiner—Donald G. Daus
Attorney, Agent, or Firm—Donald E. Gillespie; Ivan Christoffel

[57] ABSTRACT

A method of treating depression with 5-(aminoalkyl)-11-phenyl-5H-dibenzo[b,e][1,4]diazepines having the formula:

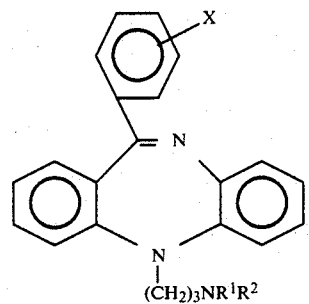

wherein $R^1$ and $R^2$ are selected from hydrogen or methyl and X is selected from hydrogen, chlorine, bromine or fluorine is disclosed.

6 Claims, No Drawings

METHOD OF TREATING DEPRESSION WITH 5-(AMINOALKYL)-11-PHENYL-5H-DIBENZO(B,E)(1,4) DIAZEPINES

REFERENCE TO PARENT APPLICATION

This application is a continuation-in-part of U.S. patent application Ser. No. 305,076 filed Sept. 24, 1981, now abandoned.

BACKGROUND OF THE INVENTION

1. Field of Invention

The present invention relates to a method of treating depression in humans with certain 5-(aminoalkyl)-11-phenyl-5H-dibenzo[b,e][1,4]diazepines. Some of the compounds are novel.

2. Description of the Prior Art

Wander, A. in British Pat. No. 907,646 discloses preparation of certain of the dibenzodiazepines utilized in the method of this invention; e.g., the active ingredient of the compound of example 1 below in the form of the maleate salt.

Wander, A. in British Pat. No. 959,994 discloses utility of reduced forms; e.g., 5-(aminoalkyl)-11-phenyl-10,11-dihydro-5H-dibenzo[b,e][1,4]diazepines as parasympathologics, antihistamines, spasmolytics, tranquilizers and psychic energizers.

Greig, M. E., et al, in J. Med. Chem. 14, No. 2 page 153 (1971) discloses anaphylaxis activity of certain dibenzodiazepine homologs in mice particularly 2-chloro-5-(dimethylaminoethyl)-11-phenyl-5H-dibenzo[b,e][1,4]diazepine.

SUMMARY OF THE INVENTION

The compounds useful in the method of treating depression in this invention have the formula:

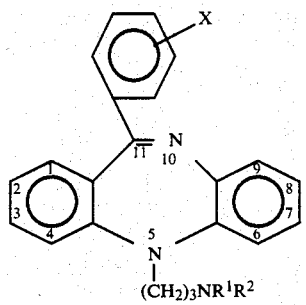

Formula I wherein
$R^1$ and $R^2$ are selected from the group consisting of hydrogen or methyl,
X is selected from the group consisting of hydrogen, chlorine, bromine or fluorine,
and the pharmaceutically acceptable acid addition salts thereof.

Compounds wherein $R^1$ and $R^2$ are both hydrogen or one is methyl and one is hydrogen are novel.

Pharmaceutically acceptable acid addition salts are those salts which are physiologically compatible, such salts being formed either by strong or weak acids. Representative of strong acids are hydrochloric, sulfuric and phosphoric acids. Representative of weak acids are fumaric, maleic, succinic, oxalic, cyclohexamic, and the like.

For the purpose of demonstrating antidepressant utility for the compounds of Formula I, the procedure given by Englehardt, E. L., et al., J. Med. Chem. 11(2): 325 (1968) which has been indicative in the past of usefulness of compounds for treating human depression was used as follows: 20 mg/kg of the compound to be testd was administered to five adult female mice (ICR-DUB strain), intraperitoneally, 30 minutes prior to the administration of a ptotic dose (32 mg/kg, I.P.) of tetrabenazine (as the methane sulfonate salt). Thirty minutes later, the presence or absence of complete eyelid closure (ptosis) was assessed in each animal. An $ED_{50}$ (Median Effective Dose) may be established for each tested compound in blocking tetrabenazine induced depression in mice, following the procedure given by Litchfield et al., J. Pharmacol. Exp. Therap. 96: 99–113 (1949). The preferred dibenzodiazepine useful in the method of this invention is the active agent of Example 1; namely, 5-(3-dimethylaminopropyl)-11-phenyl-5H-dibenzo[b,e][1,4]diazepine.

It is therefore an object to provide a method of treating depression and pharmaceutical compositions therefor.

Additional objects and advantages of the present invention will be apparent to one skilled in the art and other will become apparent from the following description of the best mode of carrying out the present invention and from the appended claims.

DETAILED DESCRIPTION OF THE INVENTION

In the method of this invention the usual dosage forms of active substance comprised of the active ingredient of Formula I with a suitable pharmaceutical carrier to provide solutions, syrups, elixirs, tablets, capsules, suppositories, powders, and the like are employed.

The compounds of Formula I wherein the 5-position is substituted by the 3-dimethylaminopropyl radical are prepared by cyclodehydration of the N-(3-dimethylaminopropyl)-o-benzamido-diphenylamines as in British Pat. No. 907,646 using a dehydrating-condensation catalyst; for example, phosphorus pentoxide or oxyhalogenides of phosphorus, preferably the latter, in a suitable solvent; e.g., 1,1,2,2-tetrachloroethane. The equation is:

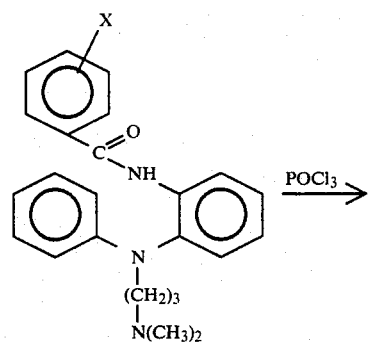

IIa

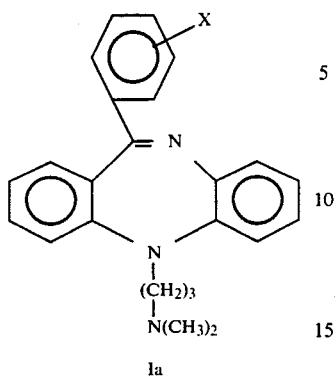

Ia wherein X has the values assigned under Formula I above.

The novel compounds of Formula I wherein the 5-position is substituted by the 3-aminopropyl radical are prepared by cyclodehydration of novel N-[3-(1-phthalimido)propyl]-o-benzamido-diphenylamines (IIb) and thereafter converting the phthalimido moiety to amino (NH₂) with hydrazine and acid. The equation is:

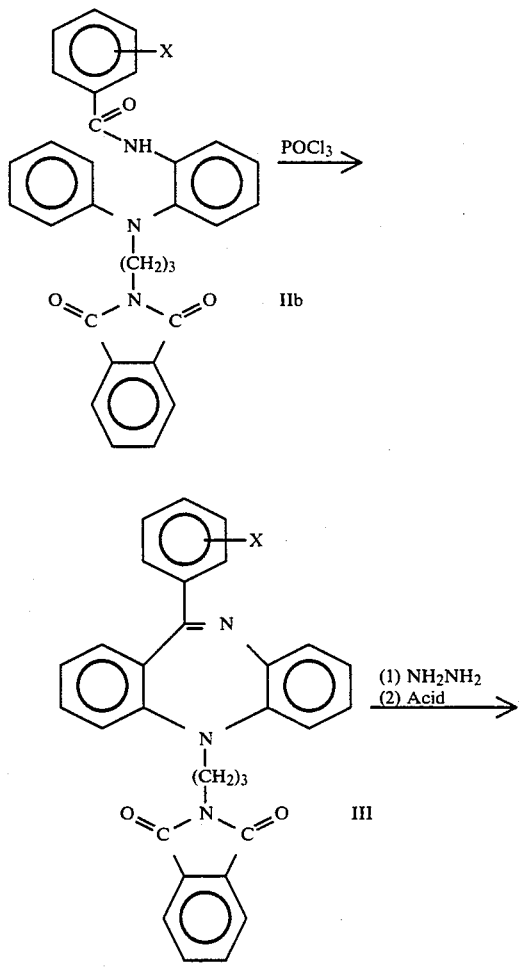

IIb

III

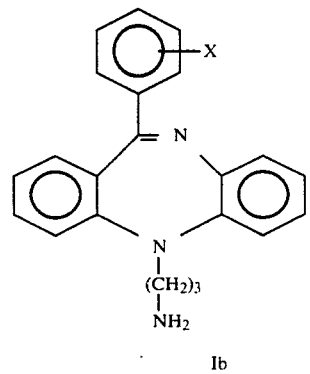

Ib wherein X has the values assigned under Formula I. Compounds of Formula III are also novel.

The novel compounds of Formula I wherein the 5-position is substituted by 3-monomethylpropyl amine are prepared by further reaction of the 3-aminopropyl compound with triethylorthoformate followed by reaction with sodium borohydride (procedure of Crocket & Blanton, 1974(1): 55-6 Synthesis). The equation is as follows:

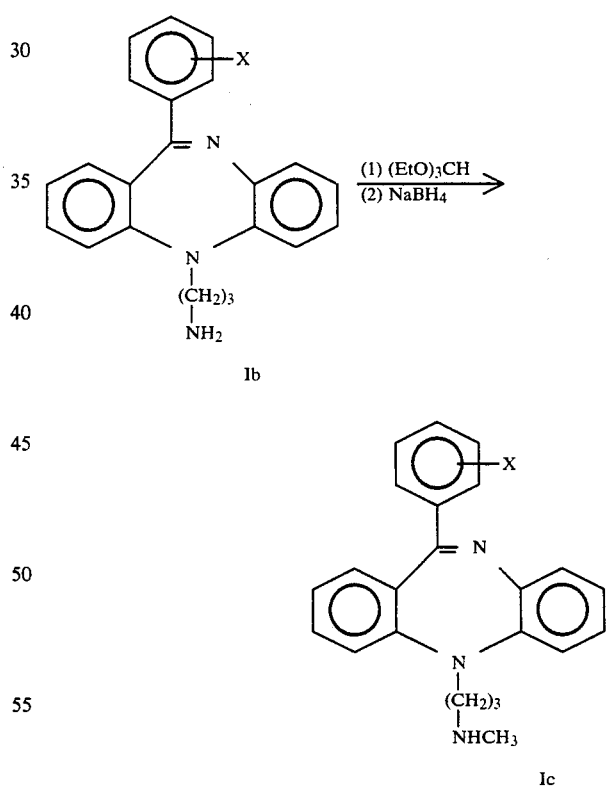

Ib

Ic

The starting benzamido compounds II (IIa and IIb) are prepared by a modification of the procedure of British Pat. No. 907,646. Ortho-nitro-diphenylamine is first reductivey alkylated with a solution of β-chloropropyl dimethylamine or 3-(1-phthalimido)-1-chloropropane and following this the nitro moiety is reduced with hydrogen over palladium on carbon to give the corresponding ortho amino compound. The amino radical in the ortho position is then reacted with benzoyl halide or a substituted benzoyl halide. The equation is as follows:

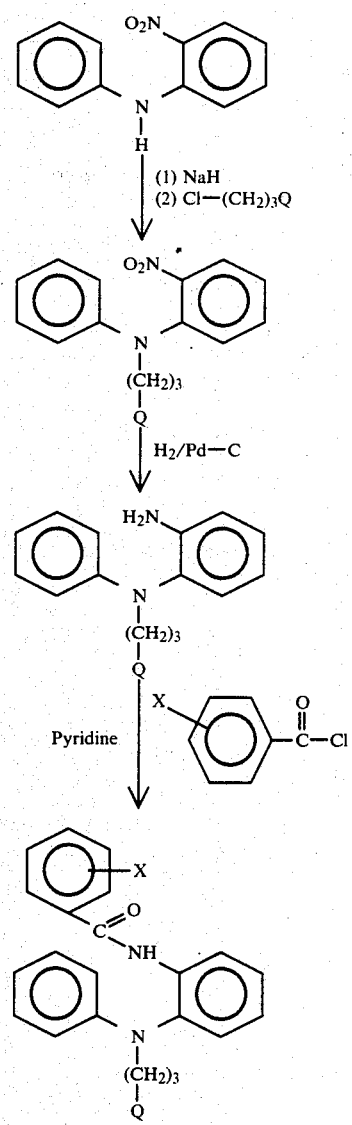

wherein Q=—N(CH$_3$)$_2$ or 1-phthalimido. and X is as defined above. Compounds of Formula II wherein Q is 1-phthalimido are also novel.

Preparation 1

N-(3-Dimethylaminopropyl)-o-nitrodiphenylamine hydrochloride

A stirred mixture of 30.0 g (0.140 mole) of 2-nitrodiphenylamine, 84.0 g (1.05 mole) of 50% sodium hydroxide, 33.0 g (0.210 mole) of 3-dimethylaminopropyl chloride hydrochloride, 4.5 g (0.014 mole) of tetrabutylammonium bromide and 60 ml of toluene was refluxed for 4 hr. The reaction mixture was cooled and diluted with 100 ml of water and 100 ml of toluene. The layers were separated and the organic phase extracted three times with 100 ml portions of 3N hydrochloric acid and once with 50 ml of water. The combined aqueous extracts were basified with 50% sodium hydroxide and extracted twice with 100 ml of methylene chloride. The combined methylene chloride extracts were washed with 50 ml water and 25 ml saturated sodium chloride solution, dried over sodium sulfate and concentrated in vacuo to give 34 g (81%) free base of the title compound. The solid was converted to the hydrochloride with hydrogen chloride and recrystallized twice from isopropyl ether-isopropyl alcohol to give yellow-gold solid, m.p. 147.5°–149° C.

Analysis: Calculated for C$_{17}$H$_{22}$N$_3$O$_2$Cl: C, 60.80; H, 6.60; N, 12.51. Found: C, 60.76; H, 6.64; N, 12.38.

Preparation 2

N-(3-Dimethylaminopropyl)-o-aminodiphenylamine

A mixture of 32.0 g (0.107 mole) of N-(3-dimethylaminopropyl)-o-nitrodiphenylamine (b.p. 155°/0.4 to 174° C./0.33 mm), 100 ml of 200 proof ethyl alcohol and 1.5 g of 10% palladium-on-carbon catalyst was shaken under hydrogen atmosphere at room temperature for one hr. After approximately the theoretical amount of hydrogen was absorbed, the catalyst was filtered off through a celite filter cake and solvent removed under reduced pressure. The residue was distilled under high vacuum as follows:

| | b.p., °C. | Amt., g |
|---|---|---|
| Fraction 1 | 80–130°/0.2 mm | 4.0 |
| 2 | 130–137°/0.2 mm | 7.0 |
| 3 | 137–142°/0.2 mm | 15.5 |

Thin layer chromatography using 20% methyl alcohol-80% benzene on silica gel, showed Fraction 3 to be quite pure.

Preparation 3

N-(3-Dimethylaminopropyl)-o-aminodiphenyl amine dihydrochloride

A mixture of 35.5 g (0.118 mole) of N-(3-dimethylaminopropyl)-o-nitrodiphenylamine (free base) in 175 ml of ethyl alcohol (95%) and 4.0 g of palladium hydroxide (20% on C) was shaken in a Parr bottle for 2 hr at room temperature under 41 psi. of hydrogen. The reaction mixture was filtered and the filtrate concentrated in vacuo. A portion of the residue (the free base) was reacted with hydrogen chloride in isopropyl alcohol-water to give the dihydrochloride salt. Recrystallization gave a beige solid, m.p. 224°–230° C. (decomp.).

Analysis: Calculated for C$_{17}$H$_{25}$N$_3$Cl$_2$: C, 59.65; H, 7.36; N, 12.28. Found: C, 59.61; H, 7.41 N, 12.27.

Preparation 4

N-(3-Dimethylaminopropyl)-o-benzamidodiphenylamine

To a solution of 15.5 g (0.0575 mole) of N-(3-dimethylaminopropyl)-o-aminodiphenylamine in 100 ml of pyridine cooled to about 5° C., under nitrogen atmosphere was added 17.8 g (0.063 mole) of benzoyl chloride. A small amount of benzene was used to wash the remaining benzoyl chloride into the reaction vessel. The mixture was stirred for 1 hr and the vessel stoppered and placed in the refrigerator over the weekend. The solvent was then evaporated under reduced pressure. The residual oil was dissolved in 100 ml of methylene chloride and the solution washed once with 150 ml of 3N sodium hydroxide and three times with 250 ml of water. The methylene chloride layer was dried over magnesium sulfate and evaporated under reduced pressure. Residual pyridine was then removed under high vacuum (0.2 mm Hg) over night. Weight of the residual oil, the free base, was 24.9 g.

Oxalate Salt—To a hot solution of 4.0 g of the free base in isopropyl alcohol was added 1.35 g (0.0107 mole) of oxalic acid dihydrate. The precipitated oxalate salt of the title compound weighed 3.5 g and melted at 162°–5° C. The salt after drying 1 hr at 97°–98° C. (refluxing propyl alcohol) and overnight at room temperature all at 0.1 mm Hg., analyzed as follows:

Analysis: Calculated for $C_{26}H_{29}N_3O_5$: C, 67.37; H, 6.31; N, 9.06. Found: C, 67.42; H, 6.35; N, 9.01.

Preparation 5

N-(3-Dimethylaminopropyl)-o-(2-fluorobenzamido)diphenylamine

To a stirred solution of 12.0 g (0.0444 mole) of N-(3-dimethylaminopropyl)-o-aminodiphenylamine, 4.7 g (0.0466 mole) of triethylamine and 150 ml of dry methylene chloride was added dropwise at 15°–20° C., 7.4 g (0.0466 mole) of 2-fluorobenzoyl chloride. The reaction mixture was stirred at room temperature for 4 hr and filtered. The filtrate was washed with 25 ml water, twice with 25 ml of 5% sodium hydroxide solution, once more with 25 ml of water, 25 ml of saturated sodium chloride solution, dried over sodium sulfate and concentrated in vacuo. The residue was triturated in isopropyl ether to give 12.5 g (72.5%) product. Recrystallization from isopropyl alcohol-isopropyl ether gave an off-white solid, m.p. 64°–65° C.

Analysis: Calculated for $C_{24}H_{26}N_3OF$: C, 73.63; H, 6.69; N, 10.73. Found: C. 73.49; H, 6.70; N, 10.61.

Preparation 6

Following the procedure of Preparation 5 and substituting the following for 2-fluorobenzoyl chloride:
2-chloro-benzoyl chloride,
3-chloro-benzoyl chloride,
3-fluoro-benzoyl chloride,
2-bromo-benzoyl chloride,
3-bromo-benzoyl chloride, and
4-chloro-benzoyl chloride,
there are obtained:
N-(3-dimethylaminopropyl)-o-(2-chlorobenzamido)diphenylamine,
N-(3-dimethylaminopropyl)-o-(3-chlorobenzamido)diphenylamine,
N-(3-dimethylaminopropyl)-o-(3-fluorobenzamido)diphenylamine,
N-(3-dimethylaminopropyl)-o-(2-bromobenzamido)diphenylamine,
N-(3-dimethylaminopropyl)-o-(3-bromobenzamido)diphenylamine, and
N-(3-dimethylaminopropyl)-o-(4-chlorobenzamido)diphenylamine.

Preparation 7

N-[3-(1-Phthalimido)propyl]-o-nitrodiphenylamine

Under nitrogen atmosphere, a solution of 53.6 g (0.25 mole) of 2-nitrodiphenyl amine in 100 ml of dry dimethylformamide was added dropwise at 30°–35° C. over a 30 minute period to a stirred suspension of 18 g (0.375 mole) of sodium hydride (50% in oil) in 100 ml of dry dimethylformamide. The mixture was stirred for 3 hr at room temperature. A solution of 80.4 g (0.30 mole) of N-(3-bromopropyl)phthalimide in 100 ml of dimethylformamide was added dropwise over a 45 minute period. The reaction mixture was stirred for 34 hr at room temperature. The excess sodium hydride was quenched by the cautious, dropwise addition of 50 ml of water and the solution was concentrated in vacuo at 90° C. The residue was partitioned between 300 ml of ethyl acetate and 400 ml of dilute aqueous sodium hydroxide. The organic phase was washed once with 100 ml of 10% sodium hydroxide solution and three times with 100 ml portions of water. The organic phase was dried over sodium sulfate and concentrated to 50 g residue. Two recryltallizations from ethyl acetate-isopropyl ether gave a bright red solid, m.p. 116°–117° C.

Analysis: Calculated for $C_{23}H_{19}N_3O_4$: C, 68.82; H, 4.77; N, 10.47. Found: C, 68.64; H, 4.76; N, 10.37.

Preparation 8

N-[3-(1-Phthalimido)propyl]-o-aminodiphenylamine

A mixture of 20 g (0.050 mole) of N-[3-(1-phthalimido)propyl]-o-nitrodiphenylamine in 225 ml of ethyl acetate-abs. ethyl alcohol (9:1) and 4.9 g of palladium hydroxide (20% on carbon) was shaken in a Parr bottle for 2¼ hr at room temperature under 37 psi. of hydrogen. The reaction mixture was filtered and the filtrate concentrated in vacuo to give 18 g of residue. A 2.0 g portion of the residue was crystallized from isopropyl alcohol-water. The solid was recrystallized from ethyl alcohol to give 1.5 g of a deep yellow solid, m.p. 103.5°–105° C.

Analysis: Calculated for $C_{23}H_{21}N_3O_2$: C, 74.38; H, 5.70; N, 11.31. Found: C, 74.01; H, 5.67; N, 11.21.

Preparation 9

N-[3-(1-Phthalimido)propyl]-o-(benzamido)diphenylamine

To a solution of 40 g (0.108 moles) of N-[3-(1-phthalimido)propyl]-o-aminodiphenylamine and 11.4 g (0.113 mole) of dry triethylamine in 200 ml of dry methylene chloride was added dropwise at 15°–20° C., 15.8 g (0.113 mole) of benzoyl chloride. The reaction mixture was stirred at room temperature for 4 hr and filtered. The filtrate was washed in sequence once with 50 ml of water, twice with 50 ml portions of 5% aqueous sodium hydroxide, once with 50 ml water and 30 ml of saturated sodium chloride solution and then dried and concentrated. The residue confirmed to be the title product by chemical ionization mass spec. analysis weighed 5 g.

Preparation 10

N-3-(1-Phthalimido)propyl-o-(2-fluorobenzamido)diphenylamine

To a stirred mixture of 36.6 g (0.099 mole) of N-[3-(1-phthamimido)propyl]-o-aminodiphenylamine, 10.5 g (0.104 mole) of triethylamine, 2 g of powdered molecular sieves and 200 ml of methylene chloride, was added dropwise at 15°–20° C., 16.3 g (0.103 mole) of 2-fluorobenzoyl chloride. The reaction mixture was stirred for 3 hr at room temperature and filtered. The filtrate was washed in sequence once with 100 ml of water, twice with 100 ml of 10% aqueous sodium hydroxide and once with 50 ml of water and then dried over sodium sulfate and concentrated in vacuo. The residue was crystallized from ethyl acetate-isopropyl ether to give 35.4 g (62.5%) title product. Recrystallization from ethyl acetate-isopropyl ether gave off-white flocculent solid, m.p. 116°–117° C.

Analysis: Calculated for $C_{30}H_{24}N_3O_3F$: C, 73.01; H, 4.90; N, 8.51. Found: C, 73.14; H, 4.88; N, 8.49.

Preparation 11

When in the procedure of Preparation 10, N-3-(1-phthalimido)propyl-o-aminodiphenylamine is reacted with each of the following acyl chlorides:
2-chloro-benzoyl chloride,
3-chloro-benzoyl chloride,
3-fluoro-benzoyl chloride,
2-bromo-benzoyl chloride,
3-bromo-benzoyl chloride, and
4-chloro-benzoyl chloride,
there are obtained:
N-3-(1-phthalimido)propyl-o-(2-chlorobenzamido)diphenylamine,
N-3-(1-phthalimido)propyl-o-(3-chlorobenzamido)diphenylamine,
N-3-(1-phthalimido)propyl-o-(3-fluorobenzamido)diphenylamine,
N-3-(1-phthalimido)propyl-o-(2-bromobenzamido)diphenylamine,
N-3-(1-phthalimido)propyl-o-(3-bromobenzamido)diphenylamine, and
N-3-(1-phthalimido)propyl-o-(4-chlorobenzamido)diphenylamine.

The following non-limiting examples will further illustrate the compounds which are useful in the practice of the method of this invention.

EXAMPLE 1

5-(3-Dimethylaminopropyl)-11-phenyl-5H-dibenzo[b,e][1,4]diazepine, fumarate [1:1]

A stirred mixture of 18.9 g (0.05 mole) of N-(3-dimethylaminopropyl)-o-benzamidodiphenylamine and 32.19 g (0.2 mole) of phosphorus oxychloride in 50 ml of 1,1,2,2-tetrachloroethane was heated at 150° C. under nitrogen atmosphere for 1.5 hr. The mixture was cooled somewhat and poured over approximately 1000 ml of crushed ice and then diluted with enough water for a final volume of 1000 ml. The aqueous suspension was extracted twice with methylene chloride and the methylene chloride layer discarded. The aqueous layer was basified with 3N sodium hydroxide and extracted with three 250 ml portions of methylene chloride. These three methylene chloride washes were combined, dried over magnesium sulfate and evaporated under reduced pressure to give a residual oil weighing 13.8 g, the free base of the title compound. The oil was dissolved in hot isopropyl alcohol and reacted with 4.5 g (0.039 mole) of fumaric acid. The fumarate salt was collected by filtration, yielding 13 g when dried, m.p. 168°–170° C.

Analysis: Calculated for $C_{28}H_{29}N_3O_4$: C, 71.32; H, 6.20; N, 8.91. Found: C, 71.19; H, 6.19; N, 8.89.

EXAMPLE 2

11-(2-Fluorophenyl)-5-(3-dimethylaminopropyl)-5H-dibenzo[b,e][1,4]diazepine fumarate hemihydrate Under nitrogen atmosphere, a solution of 7.56 g (0.0193 mole) of N-(3-dimethylaminopropyl)-o-(2-fluorobenzamido)diphenylamine and 24.7 g (0.161 mole) of phosphorus oxychloride was refluxed for 16 hr. The reaction mixture was cooled and cautiously poured, portionwise, over 50 g of ice and the mixture was stirred for 15 min. The solution was basified with conc. ammonium hydroxide and extracted three times with 50 ml of methylene chloride. The combined methylene chloride extracts were washed with 50 ml of water, 30 ml of saturated sodium chloride solution, dried over sodium sulfate and concentrated in vacuo. The residue was converted to the fumarate salt and the salt recrystallized three times from isopropyl alcohol-isopropyl ether. Further recrystallization twice from methyl cyanide-water gave 2 g of yellow solid, m.p. 155°–159° C. (after phase change at 145°–150° C.).

Analysis: Calculated for $C_{56}H_{58}N_6O_9F$: C, 67.46; H, 5.86; N, 8.43. Found: C, 67.88; H, 5.68; N, 8.44.

EXAMPLE 3

Following the procedure of Example 2 and substituting equal molar amounts of the following for N-(3-dimethylaminopropyl)-o-2-fluorobenzamidodiphenylamine:
N-(3-dimethylaminopropyl)-o-(2-chlorobenzamido)diphenylamine,
N-(3-dimethylaminopropyl)-o-(3-chlorobenzamido)diphenylamine,
N-(3-dimethylaminopropyl)-o-(3-fluorobenzamido)diphenylamine,
N-(3-dimethylaminopropyl)-o-(2-bromobenzamido)diphenylamine,
N-(3-dimethylaminopropyl)-o-(3-bromobenzamido)diphenylamine, and
N-(3-dimethylaminopropyl)-o-(4-chlorobenzamido)diphenylamine,
there are obtained:
11-(2-chlorophenyl)-5-(3-dimethylaminopropyl)-5H-dibenzo[b,e][1,4]diazepine, fumarate,
11-(3-chlorophenyl)-5-(3-dimethylaminopropyl)-5H-dibenzo[b,e][1,4]diazepine, fumarate,
11-(3-fluorophenyl)-5-(3-dimethylaminopropyl)-5H-dibenzo[b,e][1,4]diazepine, fumarate,
11-(2-bromophenyl)-5-(3-dimethylaminopropyl)-5H-dibenzo[b,e][1,4]diazepine, fumarate,
11-(3-bromophenyl)-5-(3-dimethylaminopropyl)-5H-dibenzo[b,e][1,4]diazepine, fumarate, and
11-(4-chlorophenyl)-5-(3-dimethylaminopropyl)-5H-dibenzo[b,e][1,4]diazepine, fumarate.

EXAMPLE 4

5-[3-(1-Phthalimido)propyl]-11-phenyl-5H-dibenzo[b,e][1,4]diazepine

Under nitrogen atmosphere, a solution of 49.0 g (0.11 mole) of N-[3-(1-phthamimido)propyl-o-(benzamido)diphenylamine, 152 g (0.99 mole) of phosphorus oxychloride and 100 ml of 1,1,2,2-tetrachloroethane was heated at 110° C. for 64 hr. The reaction mixture was cooled to 10° C. and cautiously poured, in portions, over 600 ml of ice. The mixture was stirred for 20 min, then basified with conc. ammonium hydroxide and extracted three times with 100 ml portions of methylene chloride. The combined methylene chloride extracts were washed with water, dried over sodium sulfate and concentrated in vacuo at 99° C. The residue was triturated with methyl alcohol to give 38.5 g (82%) product. A portion was recrystallized from acetone followed by recrystallization from acetone-methylene chloride to give mustard yellow solid, m.p. 192°–194° C.

Analysis: Calculated for $C_{30}H_{23}N_3O_2$: C, 78.76; H, 5.07; N, 9.18. Found: C, 78.44; H, 5.02; N, 9.10.

EXAMPLE 5

5-[3-(1-Phthalimido)propyl]-11-(2-fluorophenyl)-5H-dibenzo[b,e][1,4]diazepine

Under nitrogen atmosphere, a solution of 28.4 g (0.0576 mole) of N-3-(1-phthalimido)propyl-o-(2- fluorobenzamido)diphenylamine, 117 g (0.765 mole) of phosphorus oxychloride and 57 ml of 1,1,2,2-tetrachloroethane was heated at 110° C. for 30 hr. The reaction mixture was cooled and cautiously poured over 300 g of ice and the mixture stirred for 20 min. The mixture was basified with conc. ammonium hydroxide and ice, stirred for one hr and extracted with two 75 ml portions of methylene chloride. The combined methylene chloride extracts were washed with water and saturated sodium chloride solution, dried over sodium sulfate and concentrated in vacuo at 100° C. The residue was crystallized from ethyl alcohol to give 26 g (95%) product. Recrystallization from ethyl alcohol-ethyl acetate gave a yellow solid, m.p. 178°–179° C.

Analysis: Calculated for $C_{30}H_{22}N_3O_2F$: C, 75.78; H, 4.66; N, 8.84. Found: C, 75.62; H, 4.72; N, 8.67.

EXAMPLE 6

When in the procedure of Example 5 the following are substituted for N-3-(1-phthalimido)propyl-o-(2-fluorobenzamido)diphenylamine:
N-3-(1-phthalimido)propyl-o-(2-chlorobenzamido)diphenylamine,
N-3-(1-phthalimido)propyl-o-(3-chlorobenzamido)diphenylamine
N-3-(1-phthalimido)propyl-o-(3-fluorobenzamido)diphenylamine,
N-3-(1-phthalimido)propyl-o-(2-bromobenzamido)diphenylamine,
N-3-(1-phthalimido)propyl-o-(3-bromobenzamido)diphenylamine, and
N-3-(1-phthalimido)propyl-o-(4-chlorobenzamido)diphenylamine,
there are obtained:
5-[3-(1-phthalimido)propyl]-11-(2-chlorophenyl)-5H-dibenzo[b,e][1,4]diazepine,
5-[3-(1-phthalimido)propyl]-11-(3-chlorophenyl)-5H-dibenzo[b,e][1,4]diazepine,
5-[3-(1-phthalimido)propyl]-11-(3-fluorophenyl)-5H-dibenzo[b,e][1,4]diazepine,
5-[3-(1-phthalimido)propyl]-11-(2-bromophenyl)-5H-dibenzo[b,e][1,4]diazepine,
5-[3-(1-phthalimido)propyl]-11-(3-bromophenyl)-5H-dibenzo[b,e][1,4]diazepine.
5-[3-(1-phthalimido)propyl]-11-(4-chlorophenyl)-5H-dibenzo[b,e][1,4]diazepine.

EXAMPLE 7

5-(3-Aminopropyl)-11-phenyl-5H-dibenzo[b,e][1,4]diazepine hydrochloride

A mixture of 0.035 mole of 5-[3-(1-phthalimido)propyl]-11-phenyl-5H-dibenzo[b,e][1,4]diazepine, 0.039 mole of hydrazine hydrate and 175 ml of 190 proof ethyl alcohol is refluxed for 2.5 hr and allowed to stand for several hours. A solution of 10 ml concentrated hydrochloric acid in 50 ml water is added to the mixture and the mixture is stirred for several hours. The mixture is filtered and the filtrate evaporated under reduced pressure. The hydrochloride salt is isolated by recrystallization from a suitable solvent and dried under reduced pressure.

EXAMPLE 8

5-(3-Aminopropyl)-11-(2-fluorophenyl)-5H-dibenzo[b,e][1,4]diazepine

A stirred suspension of 24.0 g (0.050 moles) of 5-[3-(1-phthalimido)propyl]-11-(2-fluorophenyl)-5H-dibenzo[b,e][1,4]diazepine, 2.8 g (0.060 moles) of hydrazine hydrate (85%) and 250 ml of 95% ethyl alcohol was refluxed for 16 hr. The solution was cooled to 30° C., 25 ml of conc. hydrochloric acid and 125 ml of water were added and the mixture was stirred at 60°–70° C. for 2 hrs. The reaction mixture was cooled and filtered and the ethanol was removed by evaporation from the filtrate. The residual aqueous mixture was filtered again and this filtrate was basified with 30 g of sodium hydroxide pellets and ice then extracted three times with 50 ml of methylene chloride. The combined methylene chloride extracts were washed with 50 ml water and 30 ml of saturated aqueous sodium chloride, dried over sodium sulfate and concentrated in vacuo. The crystalline residue weighing 18 g was recrystallized from isopropyl alcohol-isopropyl ether (charcoaled) to give 9.5 g. From the filtrate, 3.5 g of yellow solid was obtained, m.p. 143.5°–145° C. Total yield was 75%.

Analysis: Calculated for $C_{22}H_{20}N_3F$: C, 76.50; H, 5.84; N, 12.16. Found: C, 76.36; H, 5.98; N, 11.86.

EXAMPLE 9

Following the procedure of Example 8 and substituting equal molar amounts of the following for 5-[3-(1-phthalimido)propyl]-11-(2-fluorophenyl-5H-dibenzo[b,e][1,4]diazepine:
11-(2-chlorophenyl)-5-[3-(1-phthalimido)propyl]-5H-dibenzo[b,e][1,4]diazepine,
11-(3-chlorophenyl)-5-[3-(1-phthalimido)propyl]-5H-dibenzo[b,e][1,4]diazepine,
11-(3-fluorophenyl)-5-[3-(1-phthalimido)propyl]-5H-dibenzo[b,e][1,4]diazepine,
11-(2-bromophenyl)-5-[3-(1-phthalimido)propyl]-5H-dibenzo[b,e][1,4]diazepine,
11-(3-bromophenyl)-5-[3-(1-phthalimido)propyl]-5H-dibenzo[b,e][1,4]diazepine, and
11-(4-chlorophenyl)-5-[3-(1-phthalimido)propyl]-5H-dibenzo[b,e][1,4]diazepine,
there are obtained:
5-(3-aminopropyl)-11-(2-chlorophenyl)-5H-dibenzo[b,e][1,4]diazepine,
5-(3-aminopropyl)-11-(3-chlorophenyl)-5H-dibenzo[b,e][1,4]diazepine,
5-(3-aminopropyl)-11-(3-fluorophenyl)-5H-dibenzo[b,e][1,4]diazepine,
5-(3-aminopropyl)-11-(2-bromophenyl)-5H-dibenzo[b,e][1,4]diazepine,
5-(3-aminopropyl)-11-(3-bromophenyl)-5H-dibenzo[b,e][1,4]diazepine, and
5-(3-aminopropyl)-11-(4-chlorophenyl)-5H-dibenzo[b,e][1,4]diazepine,

EXAMPLE 10

N-Methyl-11-phenyl-5H-dibenzo[b,e][1,4]diazepin-5-propanamine, hydrochloride

The hydrochloride salt of 5-(3-aminopropyl)-11-phenyl-5H-dibenzo[b,e][1,4]diazepine is converted to the free base by partitioning between dilute sodium hydroxide and methylene chloride, drying and concentrating the methylene chloride layer to dryness, adding dry benzene and again concentrating to drive off the benzene. The resulting free base is dissolved in a large excess of freshly distilled triethylorthoformate with refluxing for several hours. The mixture is concentrated in vacuo, ethanol is added and the mixture concentrated again. The resulting imidate is dissolved in ethanol and sodium borohydride is added with stirring at 15°–20° C.

until thinlayer chromatography indicates the absence of substantial amount of starting material. The mixture is cooled and gradually flooded with water followed by extraction with ethyl acetate. The ethyl acetate layer is washed to neutrality and salted, filtered and evaporated. Crude free base is isolated by column chromatography and reacted with ethereal hydrogen chloride and recrystallized to give the title compound.

EXAMPLE 11

N-Methyl-11-(2-fluorophenyl)-5H-dibenzo[b,e][1,4-]diazepin-5-propanamine oxalate [1:1]

Under nitrogen atmosphere, a solution of 10.0 g (0.029 mole) of 5-(3-aminopropyl)-11-(2-fluorophenyl)-5H-dibenzo[b,e][1,4]diazepine in 150 ml of freshly distilled triethylorthoformate was refluxed for 10 hrs. The cooled solution was concentrated in vacuo. The residue was dissolved in 100 ml of absolute ethanol and the solution concentrated in vacuo. The residue was dissolved in 200 ml of absolute ethanol and the solution cooled to 27° C. Sodium borohydride, 7.8 g, was added and the mixture was stirred at room temperature for 80 hrs. A second portion of 3 g sodium borohydride was added. The reaction mixture was stirred at 35° C. for 1.25 hr and then refluxed for one hour. After cooling the reaction mixture, 70 ml of water was added portionwise. The mixture was diluted with 600 ml of water and extracted three times with 75 ml ether. The combined ether extracts were washed repeatedly with water until a neutral pH of the wash was obtained. The ether solution was dried over sodium sulfate and concentrated in vacuo to give 12.5 g of residue. The residue was purified on a 4.5×45 cm column of alumina (neutral) eluting by gradient with mixture of methyl alcohol-methylene chloride in the following manner:

| Fractions | Volume, liters | Solvent Composition methyl alcohol; methylene chloride |
| --- | --- | --- |
| 1–12 | 6.5 | 1.25:98.75 |
| 13–20 | 4.5 | 2.5:97.5 |
| 21–22 | 1.0 | 3.75:96.25 |
| 23–24 | 1.0 | 5.95:94.05 |
| 25–26 | 1.0 | 7.5:92.5 |
| 27 | 0.5 | 10:90 |

Fractions 14–27 were combined and concentrated in vacuo to give 3.2 g residue. The residue was converted to the oxalate salt and twice recrystallized from isopropyl alcohol-isopropyl ether. Light yellow solid weighing 2.0 g, m.p. 190°–192° C. (decomp.) was obtained.

Analysis: Calculated for $C_{25}H_{24}N_3O_4F$: C, 66.80; H, 5.38; N, 9.35. Found: C, 66.77; H, 5.35; N, 9.32.

EXAMPLE 12

Following the procedure of Example 11 and substituting equal molar amounts of the following for 5-(3-aminopropyl)-11-(2-fluorophenyl)-5H-dibenzo[b,e][1,4-]diazepine:
5-(3-aminopropyl)-11-(2-chlorophenyl)-5H-dibenzo[b,e][1,4]diazepine,
5-(3-aminopropyl)-11-(3-chlorophenyl)-5H-dibenzo[b,e][1,4]diazepine,
5-(3-aminopropyl)-11-(3-fluorophenyl)-5H-dibenzo[b,e][1,4]diazepine,
5-(3-aminopropyl)-11-(2-bromophenyl)-5H-dibenzo[b,e][1,4]diazepine,
5-(3-aminopropyl)-11-(3-bromophenyl)-5H-dibenzo[b,e][1,4]diazepine, and
5-(3-aminopropyl)-11-(4-chlorophenyl)-5H-dibenzo[b,e][1,4]diazepine,
there are obtained:
11-(2-chlorophenyl)-N-methyl-5H-dibenzo[b,e][1,4-]diazepin-5-propanamine oxalate,
11-(3-chlorophenyl)-N-methyl-5H-dibenzo[b,e][1,4-]diazepin-5-propanamine oxalate,
11-(3-fluorophenyl)-N-methyl-5H-dibenzo[b,e][1,4-]diazepin-5-propanamine oxalate,
11-(2-bromophenyl)-N-methyl-5H-dibenzo[b,e][1,4-]diazepin-5-propanamine oxalate,
11-(3-bromophenyl)-N-methyl-5H-dibenzo[b,e][1,4-]diazepin-5-propanamine oxalate, and
11-(4-chlorophenyl)-N-methyl-5H-dibenzo[b,e][1,4-]diazepin-5-propanamine oxalate.

Formulation and Administration

Effective quantities of the foregoing pharmacologically active compounds of Formula I may be administered to humans for therapeutic purposes according to usual modes of administration and in usual forms, such as orally in solutions, emulsions, suspensions, pills, tablets and capsules, in pharmaceutically acceptable carriers and parenterally in the form of sterile solutions.

Exemplary of solid carriers for oral administration are such as lactose, magnesium, stearate, terra alba, sucrose, talc, stearic acid, gelatin, agar, pectin or acacia.

Exemplary of liquid carriers for oral administration are vegetable oils and water.

For intramuscular administration the carrier or excipient may be a sterile, parenterally acceptable liquid; e.g., water or a parenterally acceptable oil; e.g., arachis oil contained in ampules.

Although very small quantities of the active materials of the present invention are effective when minor therapy is involved or in cases of administration to subjects having a relatively low body weight, unit dosages are usually from five milligrams or above and preferably 10, 25, 50, or 100 milligrams or even higher, preferably administered three or four times per day, depending, of course, upon the emergency of the situation, the compound used, and the particular result desired. Twenty-five to 200 milligrams appears optimum per unit dose or usual broader ranges appear to be about 10 to 500 milligrams per unit dose. Daily dosages usually required should range from about 0.5 to about 20 mg/kg/day, preferably 0.5 to 10 mg/kg. The active ingredients of the invention may be combined with other pharmacologically active agents as stated above. It is only necessary that the active ingredient constitute an effective amount; i.e., such that a suitable effective dosage will be obtained consistent with the dosage form employed. Obviously, several unit dosage forms may be administered at about the same time. The exact individual dosages as well as daily dosages will, of course, be demonstrated according to standard medical principles under the direction of a physician or veterinarian.

The following formulations are representative for the pharmacologically active compounds of this invention.

FORMULATIONS

1. Capsules

Capsules of 10 mg and 50 mg of active ingredient per capsule are prepared. With the higher amounts of active ingredient, reduction may be made in the amount of lactose.

| Typical blend for encapsulation | 10 mg. Per Capsule | 50 mg. Per Capsule |
| --- | --- | --- |
| Active ingredient, as salt | 10 | 50 |
| Lactose | 259 | 219 |
| Starch | 126 | 126 |
| Magnesium stearate | 4 | 4 |
| Total | 399 | 399 |

Additional capsule formulations preferably contain a higher dosage of active ingredient and are as follows:

| Ingredients | 100 mg. per Capsule | 250 mg. per Capsule | 500 mg. per Capsule |
| --- | --- | --- | --- |
| Active ingredient, as salt | 100 | 250 | 500 |
| Lactose | 209 | 163 | 95 |
| Starch | 87 | 81 | 47 |
| Magnesium stearate | 4 | 6 | 8 |
| Total | 400 | 500 | 650 |

In each case, uniformly blend the selected active ingredient with lactose, starch, and magnesium stearate and encapsulate the blend.

2. Tablets

A typical formulation for a tablet containing 5.0 mg of active ingredient per tablet follows. The formulation may be used for other strengths of active ingredient by adjustment of weight of dicalcium phosphate.

|  | Per Tablet, mg. |
| --- | --- |
| 1. Active ingredient | 10.0 |
| 2. Corn starch | 15.0 |
| 3. Corn starch (paste) | 12.0 |
| 4. Lactose | 35.0 |
| 5. Dicalcium phosphate | 132.0 |
| 6. Calcium stearate | 2.0 |
| Total | 206.0 |

Uniformly blend 1, 2, 4 and 5. Prepare 3 as a 10 percent paste in water. Granulate the blend with starch paste and pass the wet mass through an 8 mesh screen. The wet granulation is dried and sized through a 12 mesh screen. The dried granules are blended with the calcium stearate and compressed.

| Injectable - 2% sterile solution |  | Per cc |
| --- | --- | --- |
| Active ingredient | mg. | 20 |
| Preservative, e.g., chlorobutanol, w/vol. percent |  | 0.5 |
| Water for injection q.s. |  |  |

Prepare solution, clarify by filtration, fill into vials, seal and autoclave.

Various modifications and equivalents will be apparent to one skilled in the art and may be made in the compounds, compositions and methods of the present invention without departing from the spirit and scope thereof, and it is therefore understood that the invention is to be limited only by the scope of the appended claims.

What is claimed is:

1. A method of treating depression which comprises administering an effective amount of a compound having the formula:

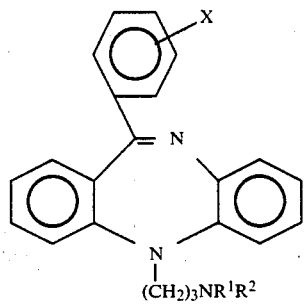

wherein
$R^1$ and $R^2$ are selected from the group consisting of hydrogen or methyl,
X is selected from the group consisting of hydrogen, chlorine, bromine or fluorine, and the pharmaceutically acceptable acid addition salts thereof.

2. The method of claim 1 wherein the compound is 5-(3-dimethylaminopropyl)-11-phenyl-5H-dibenzo[b,e][1,4]diazepine.

3. The method of claim 1 wherein the compound is 5-(3-dimethylaminopropyl)-11-phenyl-5H-dibenzo[b,e][1,4]diazepine, fumarate [1:1].

4. The method of claim 1 wherein the compound is 5-(3-aminopropyl)-11-(2-fluorophenyl)-5H-dibenzo[b,e][1,4]diazepine.

5. The method of claim 1 wherein the compound is N-methyl-11-(2-fluorophenyl)-5H-dibenzo[b,e][1,4]diazepin-5-propanamine or its oxalate salt.

6. The method of claim 1 wherein the compound is 11-(2-fluorophenyl)-5-(3-dimethylaminopropyl)-5H-dibenzo[b,e][1,4]diazepine or its fumarate hydrate salt.

* * * * *